United States Patent [19]

Howng

[11] Patent Number: 4,677,415

[45] Date of Patent: Jun. 30, 1987

[54] CERAMIC HUMIDITY SENSOR

[75] Inventor: Wei-Yean Howng, Albuquerque, N. Mex.

[73] Assignee: Motorola, Inc., Schaumburg, Ill.

[21] Appl. No.: 732,250

[22] Filed: May 8, 1985

[51] Int. Cl.⁴ .......................... H01B 1/06; H01L 7/00
[52] U.S. Cl. ........................................ 338/35; 338/34; 252/520
[58] Field of Search .................... 338/34, 35, 308, 314; 200/61.06, 61.04; 219/10.55; 314/65 R; 501/64; 340/601, 602; 252/520, 521

[56] References Cited

U.S. PATENT DOCUMENTS

| 1,720,381 | 7/1929 | Simpson | 338/57 |
| 4,015,230 | 3/1977 | Nitta et al. | 338/35 |
| 4,080,564 | 3/1978 | Nitta et al. | 324/65 R |
| 4,162,631 | 7/1979 | Logothetis et al. | 73/362 AR |
| 4,231,254 | 11/1980 | Logothetis et al. | 73/362 AR |
| 4,328,478 | 5/1982 | Murata et al. | 338/35 |
| 4,357,426 | 11/1982 | Murata et al. | 338/35 X |

FOREIGN PATENT DOCUMENTS

| 2429866 | 1/1975 | Fed. Rep. of Germany | 338/22 R |
| 2605804 | 9/1976 | Fed. Rep. of Germany | 338/22 R |
| 2838508 | 3/1980 | Fed. Rep. of Germany | 338/22 R |
| 0107696 | 9/1978 | Japan | 338/22 R |
| 0138096 | 12/1978 | Japan | 338/22 R |
| 0013409 | 4/1980 | Japan | 338/22 R |
| 0151301 | 11/1980 | Japan | 338/25 |
| 0151302 | 11/1980 | Japan | 338/25 |
| 0066745 | 6/1981 | Japan | |
| 0083901 | 7/1981 | Japan | 338/35 |
| 0010203 | 1/1982 | Japan | |
| 0575718 | 10/1977 | U.S.S.R. | 338/22 R |
| 0995130 | 2/1983 | U.S.S.R. | 338/25 |

Primary Examiner—Harold Broome
Assistant Examiner—Linda M. Peco
Attorney, Agent, or Firm—Charles L. Warren

[57] ABSTRACT

A device for monitoring humidity as a function of electrical resistance comprises a humidity-sensitive resistor formed of a ceramic including lanthanum chromite, with or without a dopant selected from titanium oxide, silicon oxide and tin oxide, and having electrodes operably affixed to the surface thereof.

20 Claims, 4 Drawing Figures

CERAMIC HUMIDITY SENSOR

TECHNICAL FIELD

The present invention relates to a device for monitoring humidity and, in particular, to a device comprising a humidity-sensitive resistor formed of a ceramic sensor element having electrodes secured to the surface thereof.

BACKGROUND OF THE INVENTION

Microwave ovens use humidity-sensitive resistors for temperature control during the heating process. It is well known, for example, that foods can be cooked in a microwave oven by controlling the cooking temperature in response to the humidity of the vapor produced as the food is heated.

However, the temperature and the relative humidity in these ovens can vary considerably depending on the ambient conditions. In addition, many conventional humidity-sensitive resistors are overly sensitive to humidity fluctuations so that temperature control in appliances using a conventional humidity-sensitive resistor is less than accurate.

Humidity can be measured by a sensor formed of a material that expands as moisture from a vapor is adsorbed. The output of such sensors is mechanical, however, and can not readily interface with an electronic signal processing device.

Another technique for sensing humidity is with a hygrometer that determines the dew point through use of a probe formed of a material, such as lithium chloride, that functions as a self-regulated heater. The relative humidity is then determined from the difference in the temperatures of the probe and the ambient atmosphere. However, this method requires rather sophisticated electronic equipment that is large and expensive.

A more preferred method of sensing humidity involves use of a porous sintered ceramic metal oxide substrate in the form of a wafer or chip that responds to humidity changes based on variations in electrical resistance (resistivity).

In particular, the adsorption and desorption of water molecules change the surface electrical conductivity of substrates formed of metal oxides. Relative to other types of humidity sensors, sintered ceramic substrates are stable in terms of physical, chemical and thermal properties.

Conventional ceramic humidity-sensitive substrates, such as $MgCr_2O_4 \cdot TiO_2$ and $Ca_{10}(PO_4)_6(OH)_2$, produce a linear semilogarithmic relationship between changes in electrical resistance and changes in relative humidity. However, the base resistance of such substrates is very high. Specifically, at lower humidity values (less than about 30 percent relative humidity), the electrical resistance becomes too high for measurement by conventional electronic circuits.

In addition to the resistance limitation, with prolonged exposure to water-containing vapors, these materials tend to form irreversible chemical complexes by hydration of the metal oxide substrate. Therefore, the sensitivity of the device is substantially reduced with time causing what is commonly referred to as an "aging effect". An external heater is often needed to regenerate the sensitivity of the device before each use. See, for example, U.S. Pat. No. 4,080,564 to Nitta et al.

Thus, a need exists for humidity-sensitive materials that respond in a predictable manner to changes in ambient humidity conditions and that operate over a wide range of relative humidity (from 0 to 100 percent). The materials should be relatively free from aging effects. The materials must also accurately measure relatively low electrical resistance values, and thus monitor humidity at low humidity ranges.

SUMMARY OF THE INVENTION

The present invention contemplates a device for monitoring the humidity of an ambient atmosphere. A preferred embodiment of the device comprises an electrical resistor that is sensitive to ambient humidity and is mounted on an insulated base member. The device preferably is contained within a metallic protective housing having a plurality of openings in the upper portion thereof for the circulation of ambient air.

The resistor of the monitoring device includes a sensor element that is in electrical communication with a pair of conductive lead wires or electrical leads. The sensor element is a ceramic having opposed, generally planar surfaces to which the electrical leads are operably affixed. The ceramic is lanthanum chromite and can include metal dopants such as $TiO_2$, $SiO_2$ and $SnO_2$. In particular, the ceramic can be represented by the formula:

$$La_aCr_bTi_xSi_ySn_zO_3$$

wherein
 $0.90 \leq a \leq 1.05$
 $b+x+y+z=1$
 $0 \leq x \leq 0.2$
 $0 \leq y \leq 0.15$
 $0 \leq z \leq 0.05$.

The electrical resistance (and the resistivity) of the ceramic and the sensor element formed therefrom is inversely proportional to relative humidity, that is, the resistance decreases as the relative humidity increases.

Specifically, the resistance of the ceramic sensor element is a linear function of the water content of an ambient gas. The term "linear function", as used herein and in the appended claims, is taken to mean a direct linear relationship between electrical resistance and humidity as well as an indirect linear relationship, i.e., a relationship between electrical resistance and humidity that is transformable into a linear relationship by an appropriate choice of variables that satisfy the generalized equation of a straight line on a coordinate chart, e.g., a semi-log plot, a log-log plot, and the like.

The relationship between electrical resistance and changes in humidity depends on the stoichiometric ratio of the elements in the composition, and the particular dopant or dopants, if any, selected. A direct linear relationship on a decimal scale of resistance to relative humidity has not been achieved by other resistive-type ceramic humidity sensors.

As a general matter, the resistivity (expressed in ohm-centimeters) of a device may be calculated from the measured resistance (ohms) and the geometrical dimensions of the device.

The electrodes of the sensor element can be formed from a material selected from the group consisting of silver (Ag), gold (Au), silver-palladium (Ag-Pd) alloys, nickel-phosphorous (Ni-P) alloys, platinum (Pt), ruthenium oxide ($RuO_2$), nickel oxide (NiO), tin oxide ($SnO_2$), indium oxide ($In_2O_3$), cadmium oxide (CdO), titanium oxide ($TiO_2$), zinc oxide (ZnO), barium titanate (BaTiO$_3$) and barium plumbate (BaPbO$_3$). Preferably, the electrodes are formed from silver (Ag), silver-palladium (Ag-Pd) alloys, platinum (Pt) or ruthenium oxide (RuO$_2$).

Accordingly, a benefit of this invention is the provision of a humidity-sensitive ceramic that can respond in a predictable manner to a change in ambient humidity conditions. The specific relationship (whether a direct linear or an indirect linear relationship as defined above) depends upon the particular confines of the ceramic composition as set forth herein. In addition, the device responds well at lower electrical resistance values, and thus can be used to monitor humidity at relatively low humidity ranges.

An advantage of this invention is the provision a humidity-sensitive resistor-containing device that responds in a reproducible and predictable manner to changes in the ambient humidity despite fluctuations in other ambient conditions. The ceramic that forms the sensor element of the device is relatively free of aging effects, and does not require the use of an external heater for regeneration after each use.

These and other benefits and advantages of this invention will better be understood from the following detailed description and the accompanying drawings.

BRIEF DESCRIPTION OF THE DRAWINGS

In the drawings, which constitute a portion of this disclosure.

DETAILED DESCRIPTION OF THE INVENTION

The present invention relates to a device for monitoring humidity and comprises a ceramic humidity-sensitive resistor.

Figure 1:
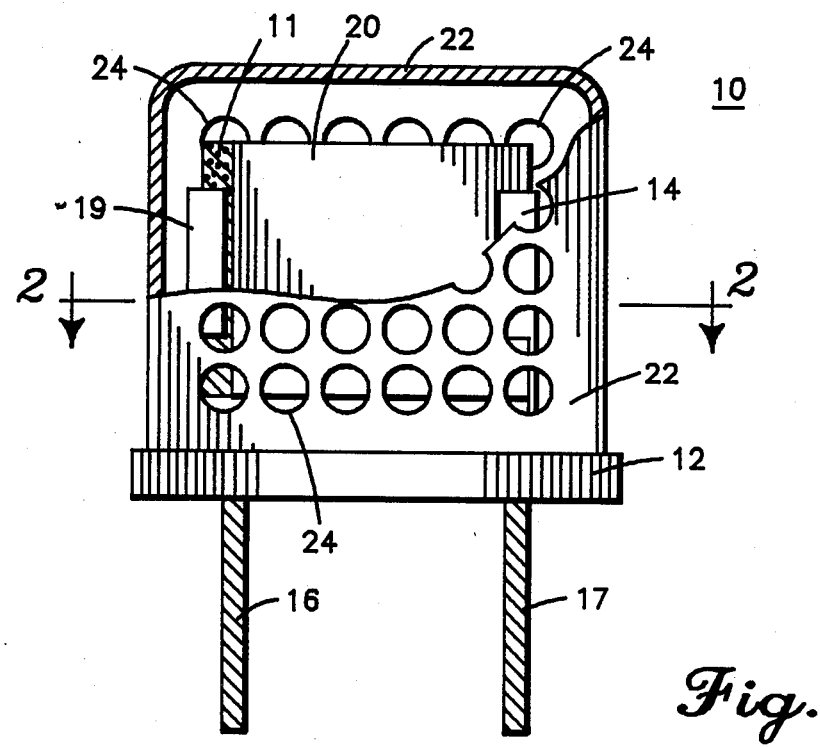
FIG. 1 is an elevational view of one embodiment of the present humidity-sensitive device with portions cut-away to show interior details.
Figure 2:
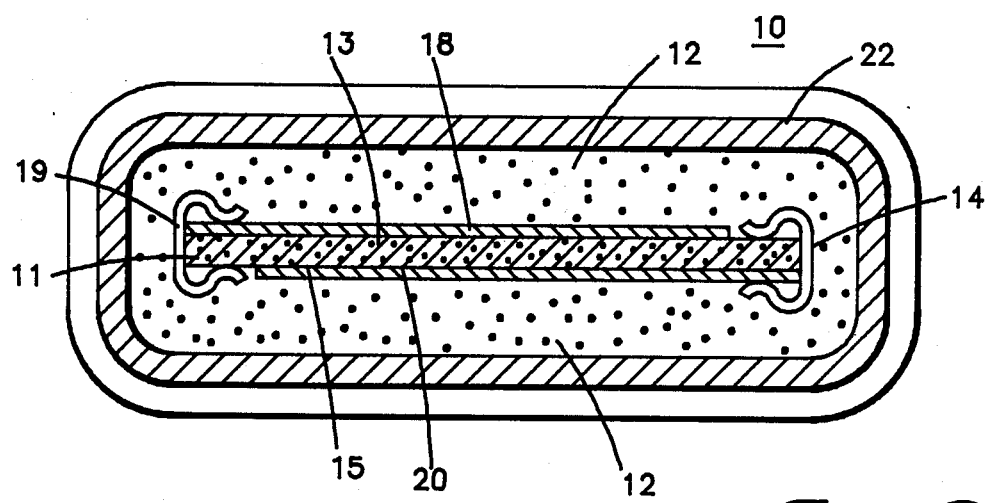
FIG. 2 is a cross-sectional view taken along the plane 2—2 shown in FIG. 1.

In particular, as shown in FIGS. 1 and 2, device 10 includes a sensor element 11 mounted on an insulated base 12 and enveloped by a housing 22 affixed to the base 12. If the base 12 and the housing 22 both are metallic, one can be affixed to the other by welding, crimping or like well-known methods. On the other hand, if the base 12 and the housing 22 are non-metallic, affixation or securement of one to the other can be achieved by gluing or the like.

A plurality of apertures 24 are provided in the housing 22 for air circulation therethrough and past the sensor element 11. Electrical leads 16 and 17 pass through the base 12 and are operably associated with the sensor element 11.

Specifically, the sensor element 11 is a porous ceramic having generally planar, opposed surfaces 13 and 15. Planar, porous electrodes 18 and 20 are in electrical contact with surfaces 13 and 15, respectively. Spring clamps 14 and 19 press electrodes 20 and 18, respectively, against their respective contiguo planar surfaces of the sensor element 11 so as to maintain electrical contact therewith. Leads 16 and 17, in turn, are in electrical contact with clamps 19 and 14, respectively.

The geometry of the sensor element 11 is such as to permit contact by an air stream, the humidity of which is to be monitored with the porous ceramic that constitutes the sensor element.

The material that serves as the sensor element can be broadly classified as a ceramic. Ceramics are compounds or compound mixtures formed by firing at high temperature or by sintering particulate metal oxides in the presence of an organic binder. The mixture can include one or more metal oxides as dopants. Ceramics are usually made by batch-mixing metal oxides, and the resultant material is expressed in mole percentages of the contained elements, rather than in terms of the molecular structure on which the physical properties of the material depend.

In particular, the invention relates to a humidity-sensing device formed of a metal oxide mixture which includes lanthanum chromite, with or without a dopant selected from the group consisting of TiO$_2$, SiO$_2$ and SnO$_2$. The composition of the ceramic mixture can be represented by the formula La$_a$Cr$_b$Ti$_x$Si$_y$Sn$_z$O$_3$ wherein
$0.90 \leq a \leq 1.05$
$b + x + y + z = 1$
$0 \leq x \leq 0.2$
$0 \leq y \leq 0.15$
$0 \leq z \leq 0.05$.

The ceramic sensor element preferably includes opposed, generally planar surfaces with conductive porous metal or metal oxide electrodes operably affixed thereto.

As the ambient relative humidity increases (or decreases), the electrical resistance of the humidity-sensitive resistor decreases (or increases) as a linear function depending on the stoichiometry of the elements in the composition and the concentration and selection of dopants.

The ceramic of the invention shows no detectable aging effect after prolonged use. Therefore, an external heating device is not needed to regenerate the sensor element.

The ceramic of the invention can be prepared by conventional ceramic processes including ball mixing. The basic criterion for processing is the provision of starting materials in a finely powdered state capable of being mixed and sintered to the desired physical form.

In particular, sintering is the high temperature fabrication of a product from a single phase wherein no intermediate reaction or new phase formation is required. As used herein, sintering means the thermal transformation of a porous compact comprising lanthanum chromite powder held together by an organic binder (with or without a metal oxide dopant) into a strong, porous, coherent material.

The processing and mixing steps in the preparation of the ceramic are well-known in the art and are generally performed in a ball mill. The component metal oxide powders are intimately mixed with water in the desired proportions, and the mixture is dried after milling for an appropriate period of time. The dried mixture is then crushed and calcined at 800°–900° C. After calcination, an organic binder (with or without water) is added to the calcined powder to combine the components of the powder into a cohesive mass.

The binder selected depends on the particular application of the resistor. Examples of suitable binders include polyvinyl chloride, polystyrene, methacrylate copolymer, polyvinyl alcohol, polyvinyl butyral and the like. As described in the following Examples, polyvinyl alcohol can be used as the binder, but such use is exemplary and is not limiting.

The cohesive mass is dried and granulated to form free flowing particles for pressing. After pressing to form a porous compact in the configuration of a thin slab, the material is sintered at about 1300 to 1400 degrees Centigrade to provide a porous ceramic.

The cohesive mass can also be tape-casted in a conventional manner onto wax paper or a glass plate and dried. The tape is then cut to form thin slabs, and the material is sintered at about 1300 to 1400 degrees Centigrade to provide a porous ceramic.

Although sintering occurs in loose powders, it is greatly enhanced by compacting the powder. As a result, most commercial sintering is performed on compacted or pressed powder mixtures, which are nevertheless porous. Compacting is generally done at room temperature, and the resulting porous compact is subsequently sintered at an elevated temperature as described above without the application of pressure.

For special applications, the powders may be compacted at an elevated pressure and thus simultaneously pressed and sintered. This is called hot pressing or sintering under pressure, and may be used in forming the ceramic substrates of the present invention.

The sintering operation involves heating the porous compact (or suspension) of the metal oxide mixture and the organic binder (where used) for a predetermined period of time at a temperature and pressure sufficient to remove the binder by pyrolysis. The time, temperature and pressure used in sintering must be sufficient to complete any chemical reactions, densify the structure, form bonds between phases and control the grain and pore sizes.

The thermodynamics of a given ceramic system can vary and should be thoroughly understood to control the manufacture of the material. The chemical composition of the powder, its particle-size distribution and its surface area are examples of important variables in the sintering process.

The suspension can be fired in the presence or absence of air. Deairing of the suspension can minimize the porosity of the final product.

During the sintering operation, the organic binder pyrolyzes. In addition, the compacted mixture shrinks uniformly, as part of the densification process that is controlled in a manner similar to that of any other ceramic or powder metallurigical process. Specifically, the relevant parameters include particle size, amount of binder, powder characterization and heating cycles. In addition to the above-listed parameters, uniformity of heating, purity of materials and controls, and handling techniques contribute to the formation of the ceramic.

Conductive electrodes can be applied to the surface of the ceramic by any suitable method, for example, by screen printing, vapor deposition, stencil or spray methods. The electrode can be applied before or after the ceramic is sintered at high temperature. If the electrode is applied after the sintering step, the assembly is cured at 700 to 1000 degrees Centigrade to provide adequate bonding between the electrode and the ceramic.

Any metal, metal oxide or metal oxide salt that provides a porous surface, strong adhesion to the ceramic, and has a lower electrical resistance than that of the ceramic can be used to form the electrodes. Such materials include silver (Ag), gold (Au), silver-palladium (Ag-Pd) alloys, nickel-phosphorous (Ni-P) alloys, platinum (Pt), ruthenium oxide ($RuO_2$), nickel oxide (NiO), tin oxide ($SnO_2$), indium oxide ($In_2O_3$), cadmium oxide (CdO), titanium oxide ($TiO_2$), zinc oxide (ZnO), barium titanate ($BaTi_3$) and barium plumbate ($BaPbO_3$). Preferable metal or metal oxides for forming the electrodes of the present invention are silver (Ag), silver-palladium (Ag-Pd) alloys, platinum (Pt) and ruthenium oxide ($RuO_2$).

After the electrode is applied, the ceramic is cured for an adequate period of time, the electrode-containing substrate is diced or cut into small sensor elements or wafers of an appropriate dimension; for example, about 10–15 millimeters square.

As indicated above, one embodiment of the humidity-sensitive resistor of the invention is formed by mounting a sensor element or a ceramic plus electrodes on an insulated base in electrical communication with two lead wires for electrical conduction. A perforated housing can be attached to the base to protect the sensor element.

The following Examples of preferred embodiments are given by way of illustration, but do not limit the scope of the invention.

EXAMPLE 1

A ceramic having the formula $La_{1.0}Cr_{0.85}Ti_{0.15}O_3$ is prepared by mixing 1.0 mole $La_2O_3$ (technical grade, obtained from Union Carbide Corp., Danbury, CT), 0.85 moles $Cr_2O_3$ (technical grade, obtained from J. T. Baker Chemical Co., Phillipsburg, NJ) 0.15 moles $TiO_2$ (technical grade, obtained from Fisher Scientific Co., Pittsburgh, PA) with about 467 milliliters of water in a ball mill for about 20 hours.

The resulting aqueous slurry is dried and crushed to fine granules for calcination. The granules have a particle size that passes through a sieve of about 200 mesh. The calcination is performed at 800–900 degress Centigrade (C) for about 2 hours. The calcined powder is then mixed with about 3.75 grams polyvinyl alcohol and is ball milled for about 3 hours.

The suspension is either spray-dried and pressed or tape-casted in a conventional manner.

Thereafter, the formed suspension or green (unsintered) body is sintered in the presence of air at about 1350 to 1400 degrees C. for 2–5 hours to form a porous ceramic.

After sintering, an electrode paste, preferably formed of Ag, Ag-Pd alloy, Pt or $RuO_2$, is screen printed on both surfaces of the ceramic and the assembly is fired at high temperature (between about 800–1000 degrees C.) for about 10 minutes.

The electrode-containing oeramic is cut or diced to form sensor elements of the desired size; for example, 5.0×5.0×0.5 cubic millimeters.

Figure 3:
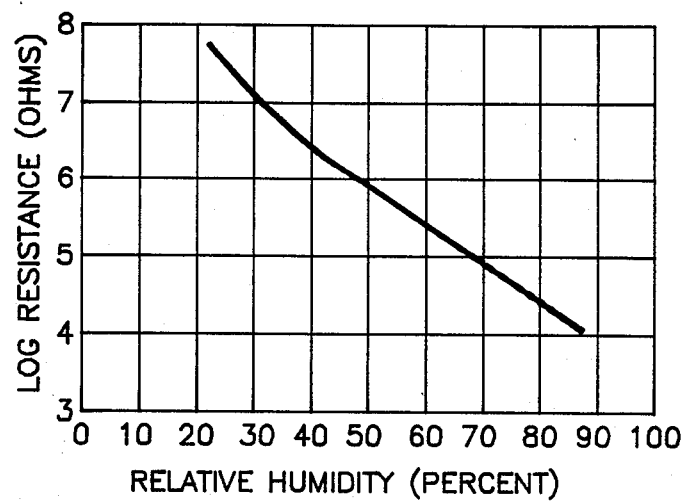
FIG. 3 is a graph that illustrates the relationship between electrical resistance on a logarithmic scale and relative humidity on a decimal scale for a sensor element having a composition represented by the formula La$_{1.0}$Cr$_{0.85}$Ti$_{0.15}$O$_3$.

FIG. 3 shows a linear relationship between the resistance (in ohms on a logarithmic scale) of $La_{1.0}Cr_{0.85}Ti_{0.15}O_3$ and the relative humidity on a decimal scale. The sensor element of this Example can be used to measure the humidity of an atmosphere for more than about 190 hours with no detectable aging effect or loss of accuracy.

EXAMPLE 2

A ceramic having the formula $La_{0.95}Cr_{0.83}Ti_{0.17}O_3$ is prepared by mixing and processing 0.95 moles $La_2O_3$, 0.83 moles $Cr_2O_3$ and 0.17 moles $TiO_2$ (all technical grade, obtained from the above-listed suppliers) as described in Example 1.

The ceramic, when formed into a sensor element according to the process described in Example 1, produces a linear relationship between resistance (on a decimal scale) as a function of relative humidity (on a logarithmic scale) and shows no detectable aging effect after more than about 400 hours of operation.

EXAMPLE 3

A ceramic having the formula $La_{0.96}Cr_{0.85}Ti_{0.15}O_3$ is prepared by mixing and processing 0.95 moles $La_2O_3$, 0.83 moles $Cr_2O_3$ and 0.15 moles $TiO_2$ (all technical grade, obtained from the above-listed suppliers) as described in Example 1.

Figure 4:
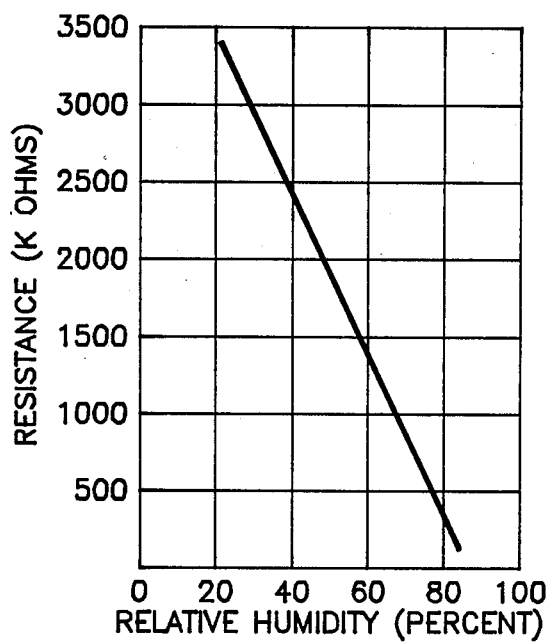
FIG. 4 is a graph that illustrates the relationship between electrical resistance on a decimal scale and relative humidity on a decimal scale for a sensor element embodying the present invention and having the composition represented by the formula La$_{0.95}$Cr$_{0.85}$Ti$_{0.15}$O$_3$.

As shown in FIG. 4, the ceramic, when formed into a sensor element according to the process described in Example 1, produces a linear relationship on a decimal scale between resistance and relative humidity. In addition, the substrate shows no detectable aging effect after more than about 400 hours of operation.

EXAMPLE 4

A ceramic having the formula $La_{1.0}Cr_{0.90}Ti_{0.10}O_3$ is prepared by mixing and processing 1.0 mole $La_2O_3$, 0.90 moles $Cr_2O_3$ and 0.10 moles $TiO_2$ (all technical grade, obtained from the above-listed suppliers) as described in Example 1.

The ceramic, when formed into a sensor element according to the process described in Example 1, produces a linear relationship on a decimal scale between resistance and relative humidity. In addition, the substrate shows no detectable aging effect after more than about 400 hours of operation.

EXAMPLE 5

A ceramic having the formula $La_{1.0}Cr_{0.83}Ti_{0.15}Si_{0.02}O_3$ is prepared by mixing and processing 1.0 mole $La_2O_3$, 0.83 moles $Cr_2O_3$, 0.15 moles $TiO_2$ and 0.02 moles $SiO_2$ (all technical grade, obtained from the above-listed suppliers) as described in Example 1.

The ceramic, when formed into a sensor element according to the process described in Example 1, produces a linear relationship on a decimal scale between resistance and relative humidity. In addition, the substrate shows no detectable aging effect after more than about 400 hours of operation.

In alternative embodiments of each of the foregoing Examples, various combinations of $TiO_2$, $SiO_2$ and $SnO_2$ can be used as dopants provided the mole percentage of titanium, silicon and tin in the resulting substrate is less than or equal to 0.2 mole percent, 0.15 mole percent and 0.05 mole percent, respectively.

In each instance, the resistance of the substrate changes as a linear function of the relative humidity. Whether that change is a direct linear relationship or an indirect linear relationship, for example, on a semi-logarithmic basis depends on the particular composition of the substrate.

While the present invention has been described with reference to the particular embodiments, it will be understood that various changes and modifications my be made without departing from the spirit of the invention.

What is claimed is:

1. A device suitable for monitoring humidity comprising a resistor which includes a ceramic sensor element having opposed, substantially planar surfaces and electrical leads operably associated with the opposed surfaces, said ceramic consisting essentially of a composition represented by the formula:

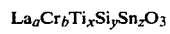
$$La_aCr_bTi_xSi_ySn_zO_3$$

wherein
$0.90 \leq a \leq 1.05$
$b+x+y+z=1$
$x+y+z>0$
$0 \leq x \leq 0.20$
$0 \leq y \leq 0.15$ 2. The device according to claim 1 wherein said ceramic includes a dopant selected from $TiO_2$, $SiO_2$ and $SnO_2$.

3. The device according to claim 1 wherein each opposed surface of the ceramic sensor element includes an electrode formed of a material selected from the group consisting of Ag, Au, Ag-Pd alloy, Ni-P alloy, Pt, $RuO_2$, NiO, $SnO_2$, $In_2O_3$, CdO, $TiO_2$, ZnO, $BaTiO_3$ and $BaPbO_3$.

4. The device according to claim 1 wherein each opposed surface of the ceramic sensor element includes an electrode formed of a material selected from the group consisting of Ag, Ag-Pd alloy, Pt and $RuO_2$.

5. The device according to claim 1 wherein the electrical resistance of said resistor is a linear function of humidity.

6. The device according to claim 1 wherein the electrical resistance of said resistor changes in a direct linear relationship to humidity.

7. The device according to claim 1 wherein the electrical resistance of said resistor changes in an indirect linear relationship to humidity.

8. The device according to claim 1 wherein the electrical resistance of said resistor changes exponentially with humidity.

9. A ceramic consisting essentially of a composition represented by the formula:

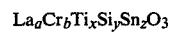
$$La_aCr_bTi_xSi_ySn_zO_3$$

wherein
$0.90 \leq a \leq 1.05$
$b+x+y+z=1$
$x+y+z>0$
$x+y+z>0$
$0 \leq x \leq 0.20$
$0 \leq y \leq 0.15$
$0 \leq z \leq 0.05$.

10. A sensor element for monitoring humidity as a function of electrical resistance comprising a ceramic having electrodes operably affixed thereon and consisting essentially of a composition represented by the formula:

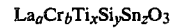
$$La_aCr_bTi_xSi_ySn_zO_3$$

wherein
$0.90 \leq a = 1.05$
$b+x+y+z=1$
$0 \leq x \leq 0.20$
$0 \leq y \leq 0.15$
$0 \leq z \leq 0.05$ the electrical resistance of said sensor element changing as a function of the humidity.

11. The sensor element according to claim 10 wherein each electrode is formed of a material selected from the group consisting of Ag, Au, Ag-Pd alloy, Ni-P alloy, Pt, RO$_2$, NiO, SnO$_2$, In$_2$O$_3$, CdO, TiO$_2$, ZnO, BaTiO$_3$ and BaPbO$_3$.

12. The sensor element according to claim 10 wherein each electrode is formed of a material selected from the group consisting of Ag, Ag-Pd alloy, Pt and RuO$_2$.

13. The sensor element according to claim 10 wherein the resistance of said ceramic is a linear function of humidity.

14. A device suitable for monitoring humidity comprising:
(a) a base;
(b) a ceramic sensor element mounted on the base;
(c) a housing provided with apertures enveloping the sensor element and affixed to the base; and
(d) electrical leads operably associated with the sensor element,
said ceramic consisting essentially of a composition represented by the formula:

$$La_a Cr_b Ti_x Si_y Sn_z O_3$$

wherein $0.90 \leq a \leq 1.05$
$b+x+y+z=1$
$x+y+z>0$
$0 \leq x \leq 0.20$
$0 \leq y \leq 0.15$
$0 \leq z \leq 0.05$.

15. The device according to claim 14 wherein said ceramic includes a dopant selected from TiO$_2$, SiO$_2$ and SnO$_2$.

16. The device according to claim 14 wherein each electrical lead is operably associated with the sensor element by an electrode formed of a material selected from the group consisting of Ag, Au, Ag-Pd alloy, Ni-P alloy, Pt, RuO$_2$, NiO, SnO$_2$, In$_2$O$_3$, CdO, TiO$_2$, ZnO, BaTiO$_3$ and BaPbO$_3$.

17. The device according to claim 14 wherein electrode formed of a material selected from the group consisting of Ag, Ag-Pd alloy, Pt and RuO$_2$.

18. The device according to claim 14 wherein the electrical resistance of said device is a linear function of humidity.

19. The device according to claim 14 wherein the electrical resistance of said device changes in a direct linear relationship to humidity.

20. The device according to claim 14 wherein the electrical resistance of said device changes in an indirect linear relationship to humidity.

* * * * *

UNITED STATES PATENT AND TRADEMARK OFFICE
CERTIFICATE OF CORRECTION

PATENT NO. : 4,677,415
DATED : June 30, 1987
INVENTOR(S) : Wei-Yean Howng

It is certified that error appears in the above-identified patent and that said Letters Patent is hereby corrected as shown below:

Column 8, after line 16 "$0 \leq y \leq 0.15$" insert --$0 \leq z \leq 0.05$.--

Column 8, line 50 "$x + y + z > 0$" delete this line.

Column 8, line 64 "$0.90 \leq a \_ 1.05$"  change "_" to --$\leq$--

Column 8, after line 65 "$b + x + y + z = 1$" insert the line --$x + y + z > 0$--.

Signed and Sealed this

Tenth Day of November, 1987

Attest:

DONALD J. QUIGG

Attesting Officer

Commissioner of Patents and Trademarks